United States Patent
Pollack et al.

(10) Patent No.: US 10,034,931 B2
(45) Date of Patent: Jul. 31, 2018

(54) USE OF EGFR PATHWAY INHIBITORS TO INCREASE IMMUNE RESPONSES TO ANTIGENS

(71) Applicant: Emory University, Atlanta, GA (US)

(72) Inventors: Brian P. Pollack, Decatur, GA (US); Richard W. Compans, Atlanta, GA (US); Joanna A. Pulit-Penaloza, Atlanta, GA (US); Ioanna Skountzou, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/024,102

(22) PCT Filed: Sep. 23, 2014

(86) PCT No.: PCT/US2014/056930
§ 371 (c)(1),
(2) Date: Mar. 23, 2016

(87) PCT Pub. No.: WO2015/042567
PCT Pub. Date: Mar. 26, 2015

(65) Prior Publication Data
US 2016/0228533 A1    Aug. 11, 2016

Related U.S. Application Data

(60) Provisional application No. 61/881,039, filed on Sep. 23, 2013.

(51) Int. Cl.
| | | |
|---|---|---|
| A61K 39/145 | (2006.01) |
| A61K 45/06 | (2006.01) |
| A61K 31/517 | (2006.01) |
| A61K 9/00 | (2006.01) |
| C12N 7/00 | (2006.01) |
| A61K 39/39 | (2006.01) |
| A61K 39/00 | (2006.01) |

(52) U.S. Cl.
CPC .......... *A61K 39/145* (2013.01); *A61K 9/0014* (2013.01); *A61K 9/0021* (2013.01); *A61K 31/517* (2013.01); *A61K 39/39* (2013.01); *A61K 45/06* (2013.01); *C12N 7/00* (2013.01); *A61K 2039/5252* (2013.01); *A61K 2039/54* (2013.01); *A61K 2039/55511* (2013.01); *A61K 2039/55516* (2013.01); *A61K 2039/572* (2013.01); *A61K 2039/575* (2013.01); *C12N 2760/16134* (2013.01); *C12N 2760/16163* (2013.01); *C12N 2760/16171* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 2010/0003253 A1 | 1/2010 | Laeremans | |
| 2010/0129401 A1* | 5/2010 | Smith | A61K 39/145 424/210.1 |

FOREIGN PATENT DOCUMENTS

| | | |
|---|---|---|
| WO | 2009030239 | 3/2009 |
| WO | 2011017799 | 2/2011 |

OTHER PUBLICATIONS

Mascia et al. Blockade of the EGF receptor induces a deranged chemokine expression in keratinocytes leading to enhanced skin inflammation. Am J Pathol. Jul. 2003;163(1):303-12.*
Eierhoff et al. The epidermal growth factor receptor (EGFR) promotes uptake of influenza A viruses (IAV) into host cells. PLoS Pathog. Sep. 9, 2010;6(9): 2-16.*
Eierhoff et al. The Epidermal Growth Factor Receptor (EGFR) Promotes Uptake of Influenza A Viruses (IAV) into Host Cells, PLoS Pathog 6(9): e1001099.
Guttman-Yassky et al. Characterisation of the cutaneous pathology in non-small cell lung cancer (NSCLC) patients reated with the EGFR tyrosine kinase inhibitor erlotinib, European Journal of Cancer 46 ( 2010 ) 2010-2019.
Kaftan et al. Delay of tympanic membrane wound healing in rats with topical application of a tyrosine kinase inhibitor, Wound Rep Reg (2008) 16 364-369.
Kawaguchi et al. Targeting EGFR and HER-2 with cetuximab- and trastuzumab mediated immunotherapy in Oesophageal squamous cell carcinoma, British Journal of Cancer (2007) 97, 494-501.
Koutsonanos et al. Delivery of subunit influenza vaccine to skin with microneedles improves immunogenicity and long-lived protection, Sci Rep. 2012, 2:357.
Mascia et al. Blockade of the EGF Receptor Induces a Deranged Chemokine Expression in Keratinocytes Leading to Enhanced Skin Inflammation, AJP, 2003, vol. 163, No. 1, 303-12.
Pastore et al. ERK1/2 Regulates Epidermal Chemokine Expression and Skin Inflammation, J Immunol 2005; 174:5047-5056.
Pollack et al. Epidermal Growth Factor Receptor Inhibition Augments the Expression of MHC Class I and II Genes, Clin Cancer Res; 17(13) 2011, 4400-13.

(Continued)

*Primary Examiner* — Michelle S Horning
(74) *Attorney, Agent, or Firm* — Emory Patent Group

(57) ABSTRACT

This disclosure relates to using EGFR pathway inhibitors in combination with compositions comprising an antigen to increase, elicit, or improve an antigen or vaccine-induced immune response. In certain embodiments, the EGFR pathway inhibitor is administered under conditions such that memory cells to the antigen are formed in a subject. In certain embodiments, the composition is a vaccine. In certain embodiments, the EGFR pathway inhibitor and vaccine are administered to the skin epidermis or dermis.

3 Claims, 4 Drawing Sheets

(56) References Cited

OTHER PUBLICATIONS

Pollack et al. EGFR inhibitors, MHC expression and immune responses, OncoImmunology 1:1, 71-74, 2012.
Pruthi et al. A phase II trial of neoadjuvant erlotinib in patients with muscle-invasive bladder cancer undergoing -adical cystectomy: clinical and pathological results, 2010, BJU International, 106, 349-356.
Pulit-Penaloza et al. A protective role of murine langerin plus cells in immune responses to cutaneous vaccination with microneedle patches, Scientific Reports, 2014, 4 : 6094.
Zaiss et al. Amphiregulin enhances regulatory T cell suppressive function via the epidermal growth factor receptor, Immunity. 2013, 38(2): 275-284.

* cited by examiner

USE OF EGFR PATHWAY INHIBITORS TO INCREASE IMMUNE RESPONSES TO ANTIGENS

CROSS-REFERENCE TO RELATED APPLICATIONS

This Application is the National Stage of International Application Number PCT/US2014/056930 filed Sep. 23, 2014, which claims priority to U.S. Provisional Application No. 61/881,039 filed Sep. 23, 2013. The entirety of each of these applications is hereby incorporated by reference for all purposes.

BACKGROUND

Safety and tolerability concerns accompanying the use of live-attenuated vaccines in young, aged, and immunocompromised populations which has led to testing the feasibility of vaccines composed of pathogenic antigen subunits, e.g., proteins that makeup the envelope or matrix of virus particles. Subunit-based vaccines lack some of the inherent innate immune stimulatory properties of whole organism-based vaccines. Multiple immunizations or the use of adjuvants may become necessary to produce memory cells after vaccination. While adjuvant approaches can successfully induce protection for some vaccines, they are not universally effective. Thus, finding improved vaccination methods that have the potential to reduce the burden of re-vaccination with enhance vaccine efficacy are needed.

Pollack et al. report epidermal growth factor receptor inhibition augments the expression of MHC class I and II genes. Clin Cancer Res, 2011, 17(13):4400-13. See also Pollack, Oncoimmunology, 2012, 1(1):71-74.

Mascia et al. report the blockade of the EGF receptor induces a deranged chemokine expression in keratinocytes leading to enhanced skin inflammation. Am J Pathol, 2003, 163:303-12. See also Guttman-Yassky et al., Eur J Cancer, 2010, 46:2010-9 and Zaiss et al., Immunity, 2013, 38:275-84. Pastore et al. report ERK1/2 regulates epidermal chemokine expression and skin inflammation. J Immunol, 2005, 174:5047-56

Koutsonanos et al. report the delivery of subunit influenza vaccine to skin with microneedles improves immunogenicity and long-lived protection. Sci Rep, 2012, 2:357. See also Pulit-Penaloza et al., Sci Rep, 2014, 4:6094.

References cited herein are not an admission of prior art.

SUMMARY

This disclosure relates to using EGFR pathway inhibitors in combination with compositions comprising an antigen to increase, elicit, or improve an antigen or vaccine-induced immune response. In certain embodiments, the EGFR pathway inhibitor is administered under conditions such that memory cells to the antigen are formed in a subject. In certain embodiments, the composition is a vaccine. In certain embodiments, the EGFR pathway inhibitor and vaccine are administered to the skin epidermis or dermis.

In certain embodiments, the disclosure relates to methods of vaccinating a subject comprising administering a vaccine in combination with a epidermal growth factor receptor (EGFR) pathway inhibitor to a subject in need thereof. In certain embodiments, the subject is at risk of, exhibiting symptoms of, or diagnosed with a pathogenic infection.

In certain embodiments, the epidermal growth factor receptor (EGFR) pathway inhibitor is an epidermal growth factor receptor (EGFR) inhibitor or a mitogen-activated protein kinase kinase 1 (MEK1) inhibitor.

In certain embodiments, the vaccine and/or epidermal growth factor receptor (EGFR) pathway inhibitor are administered locally to the skin.

In certain embodiments, the administered locally to the skin is topically administered or intradermally administered.

In certain embodiments, the vaccine comprises a live, killed, or attenuated virus, a virus particle, virus-like particle, or virosome.

In certain embodiments, the vaccine comprises a polypeptide sequence expressed by a pathogen. In certain embodiments, the polypeptide sequence is a viral envelope protein or matrix protein.

In certain embodiments, the disclosure relates to compositions comprising an EGFR inhibitor and an antigen. In certain embodiments, antigen comprises a polypeptide sequence expressed by a pathogen. In certain embodiments, the polypeptide sequence is a viral envelope protein or matrix protein.

In certain embodiments, the disclosure relates to vaccinations against cancer, with a cancer antigen for anti-cancer vaccination and used related thereto such as against skin cancers such as melanoma. In certain embodiments, the antigen is a melanoma-associated antigen, MAGE protein or fragment such as gp100, Melan-A, tyrosinase and the cancer-testis antigens MAGE-A1, MAGE A4, and NY-ESO-1.

DETAILED DESCRIPTION

Figure 1:
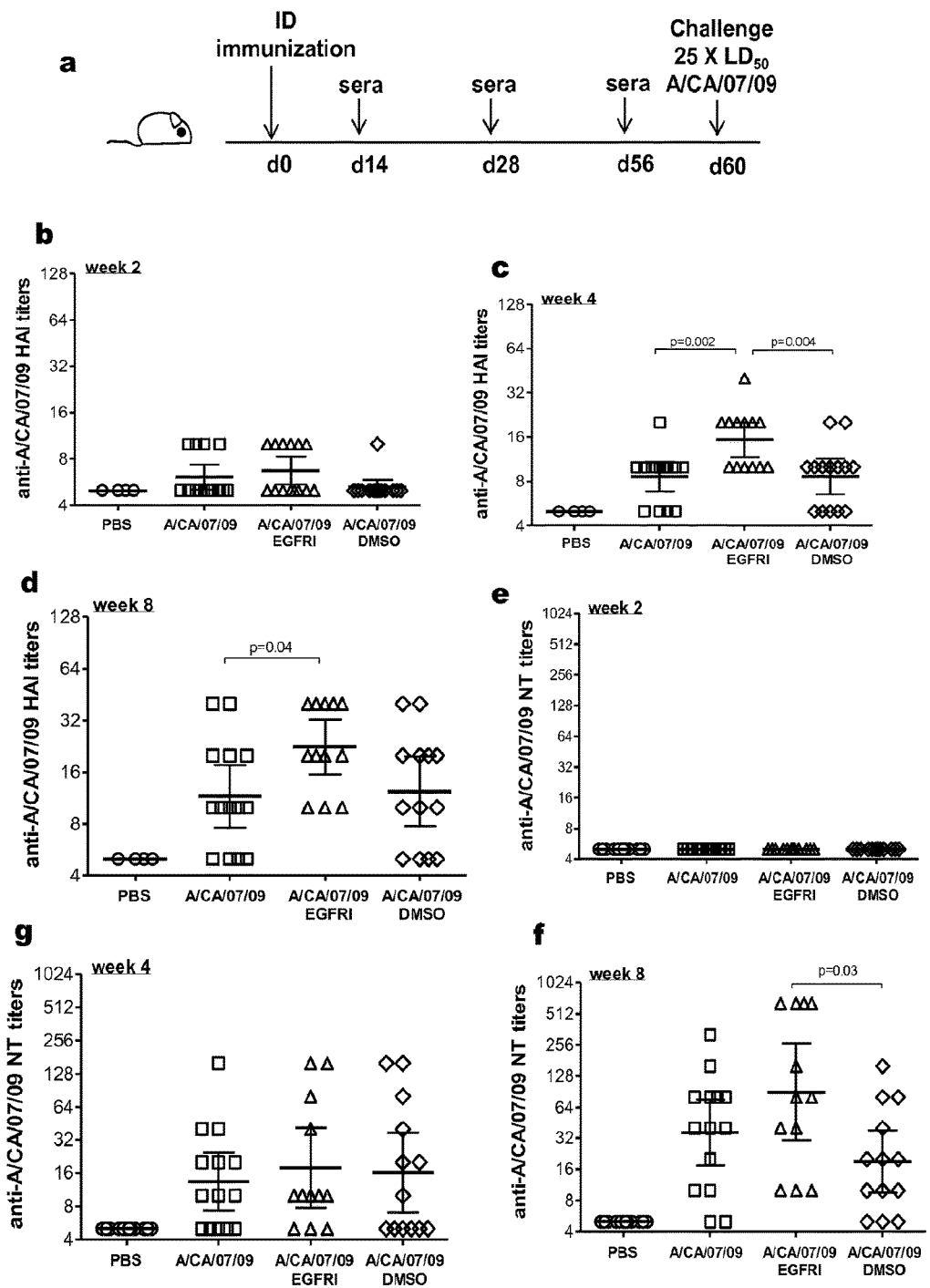
FIG. 1 shows data indicating topical application of EGFR inhibitor enhances humoral responses to intradermally injected influenza vaccine. A single application of the EGFR inhibitor (PD168393) at the site of and just prior to intradermal vaccination induced significantly higher functionally relevant humoral immune responses than those seen in vehicle (10% DMSO in ethanol)-treated mice.
Figure 2:
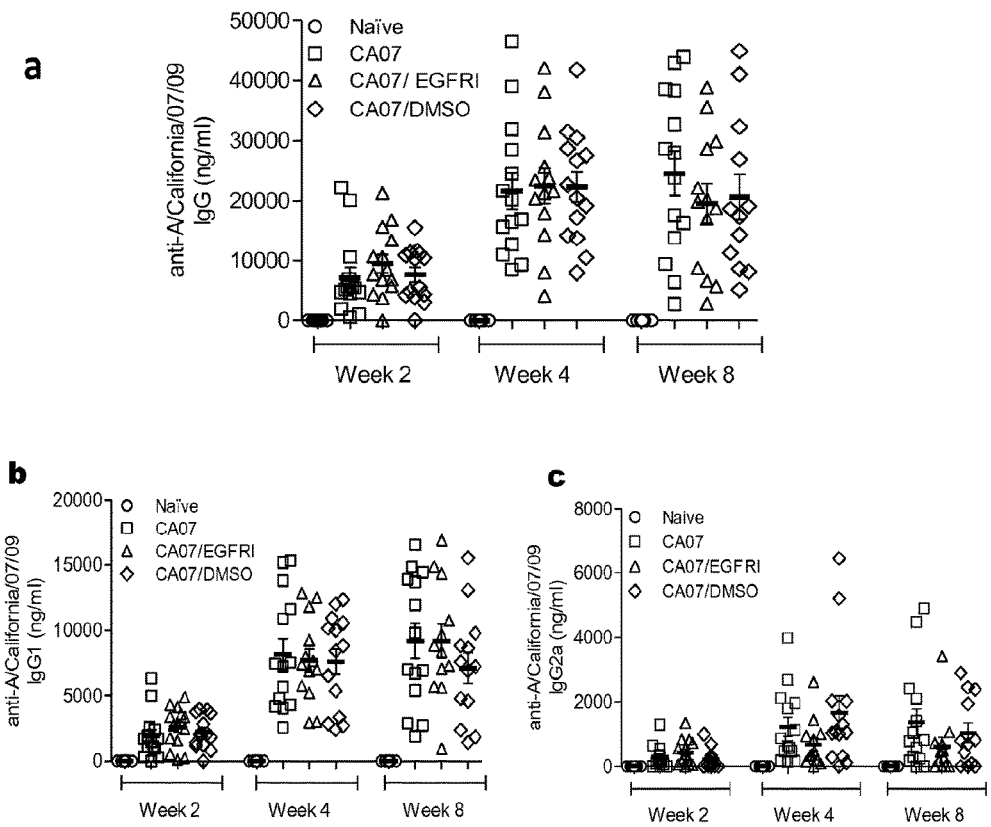
FIG. 2 shows data indicating the impact of topical application of an EGFRI on humoral responses to influenza vaccination. Levels of influenza-specific binding IgG antibodies in sera of vaccinated mice are shown.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

A "subject" refers to a human, animal, laboratory animal, livestock, or domestic pet.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

A "vaccine" refers to a preparation of immunogenic material capable of stimulating an immune response, administered for the prevention, amelioration, or treatment of infectious pathogens. The immunogenic material may include live-attenuated or killed microorganisms (such as bacteria or viruses), or antigenic proteins, peptides or nucleic acids derived from them. In some cases, the vaccine is a subunit vaccine, which is an immunizing agent that has been treated to remove traces of nucleic acid (such as viral nucleic acid) so that only protein subunits remain. The subunits have less risk of causing adverse reactions. The vaccine can also be a live vaccine, which is a vaccine prepared from living attenuated organisms or from viruses that have been attenuated, e.g., slowed replication, but can still replicate in the cells of the host organism. Vaccines may elicit both prophylactic (preventative) and therapeutic responses. Methods of administration vary according to the vaccine, but may include inoculation, ingestion, inhalation or other forms of administration.

A "pathogen" refers to biological agent that causes disease or illness to its host. Pathogens include, for example, bacteria, viruses, fungi, protozoa and parasites. Pathogens are also referred to as infectious agents or infectious microorganisms.

Examples of pathogenic viruses include, but are not limited to those in the following virus families: Retroviridae (for example, human immunodeficiency virus (HIV), human T-cell leukemia viruses; Picornaviridae (for example, polio virus, hepatitis A virus, hepatitis C virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus), rubella viruses); Flaviridae (for example, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses, including avian flu and swine flu); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus).

Examples of bacterial pathogens include, but are not limited to: *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

Examples of fungal pathogens include, but are not limited to: *Cryptococcus neoformans, Histoplasma capsulatum, Coccidioides immitis, Blastomyces dermatitidis, Chlamydia trachomatis, Candida albicans*.

Other pathogens (such as parasitic pathogens) include, but are not limited to: *Plasmodium falciparum, Plasmodium vivax, Trypanosoma cruzi* and *Toxoplasma gondii*.

An "adjuvant" refers to a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

An "antigen" refers to a compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. Antigen-specific T cells are T cells that are capable of specifically recognizing (via T cell receptors) and responding to an antigen. As used herein, "enhancing" an antigen-specific T cell response includes, but is not limited to, increasing the number, quality and/or activity of T cells, such as CD4+ and/or CD8+ memory T cells. There are three phases of an antigen-specific CD8+ T cell response after exposure to antigen (such as during a viral infection). First, during the expansion phase naïve antigen-specific CD8+ T cells exponentially expand and become effector T cells. These effector T cells stop proliferating approximately 1 to 2 weeks after exposure and enter the contraction phase. During the contraction phase, effector CD8+ T cells gradually acquire memory T cell phenotype and function. The contraction phase is also referred to as the "cell death phase" as a significant number of activated T cells (often about 90%) die during this phase. The maintenance phase, which is also referred to as the "memory phase," follows the contraction phase and is characterized by long-term survival, e.g., more than one or two years, of antigen-specific memory cells. Immunological memory may involve T and/or B cells and typically results in a faster secondary antibody response with the secretion of non-IgM isotypes of Ig.

A "polypeptide" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced. In certain contexts, term polypeptide refers to a portion or fragment of a polypeptide that exhibits at least one useful epitope. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen.

A "virus particle" refers to particle containing a coat of proteins, e.g., matrix proteins, which are typically used to surround viral nucleic acids. A "virion" refers to a virus particle comprising a live, or optionally attenuated, virus. Virus particles can have a lipid membrane, e.g., lipid bilayer, which envelopes the protein coat, e.g., derived from a cell membrane during infection. The viral genome may encode proteins that are externally exposed in the lipid membrane, i.e., envelope proteins.

A "virus-like particle (VLP)" refers to a particle that contains viral proteins, but they do not contain intact viral genomic material; they are non-infectious. VLPs may express envelope proteins or glycoproteins on the surface of the VLP. VLPs can be produced by in vitro cell culture expression systems such as, but not limited to, a recombinant baculovirus expression system or a recombinant pox-virus expression system. See, e.g., Yamshchikov et al., Virology, 214, 50-58, (1995) and Wyatt L S, et al., Vaccine, 15, 1451-8, (1996).

A "virosome" refers to a particle that contains a lipid membrane (mono- or bi-layer) and viral envelope proteins, e.g., a reconstituted membrane of an enveloped virus. Virosomes may additionally carry adjuvants and antigens from other sources such as other pathogens. See, e.g., Stegmann et al., Vaccine, 2010, 28(34):5543-50. Engineered virosome vaccines typically retain the receptor binding and membrane fusion activities of live virus enabling the virosomes to enter APCs by receptor-mediated endocytosis leading to MHC antigen presentation and T cell responses.

Topical Application of an Epidermal Growth Factor Receptor Kinase Inhibitor Enhances the Response to Vaccination In certain embodiments, the disclosure relates to the use of kinase inhibitors of the EGF receptor to modulate the immune response to a vaccination. Using influenza vaccination as an example platform, a single application of an EGF receptor inhibitor (EGFRI) at a vaccination site was found to enhances the generation of protective antibodies, increase immune cell activation within skin draining lymph nodes, and attenuate viral loads within the lungs of mice following influenza challenge. Experiments performed herein provide evidence that immune effects can be exploited locally to enhance the induction of antigen-specific immune responses.

In certain embodiments, it is contemplated that the EGFRI vaccination approach may be utilized in microneedle-based system and epicutaneous vaccination approaches. In certain embodiments, the vaccine, antigen, and/or EGFR pathway inhibitor is administered via conventional hypodermic injection or microneedles. In certain embodiments, the microneedles are a biocompatible polymer, e.g., polyvinylpyrrolidone (PVP), encapsulating a vaccine and/or EGFR pathway inhibitor for insertion and dissolution in the skin. See, e.g., Sullivan et al., Nat Med, 2010, 16(8):915-20.

In certain embodiments, the disclosure contemplates topical and microneedle-based influenza vaccination that leads to the induction of long-lasting protective immune responses in animals. Due to antigenic variation in influenza viral glycoproteins annual vaccination is recommended to protect the population against infection and disease progression particularly the young, aged and immunocompromised groups.

In experiments disclosed herein, an EGFR inhibitor, PD168393 was concomitantly administered with A/California/07/09 subunit influenza vaccine in murine skin, and this significantly enhanced influenza-specific neutralizing antibody titters and cellular immune responses resulting in improved protective immunity of the challenged vaccinated group indicating that kinase inhibitors can been used as an adjuvant to modulate vaccine-induced immune responses. In addition, this indicates that the immune response to a vaccine can be enhanced by disrupting a specific signal transduction pathway that is active within the skin.

The use of inhibitor-based adjuvants (IBAs) alone or in combination with other adjuvants represents an approach to enhance the local production of chemokines and cytokines by exploiting and enhancing the ability of resident skin cells to express these molecules. Topical application of an IBA may be uses with vaccines that are administered onto or just beneath the skin surface via topical application and/or microneedle-based approaches.

Although it is not intended that embodiments of the disclosure be limited by any particular mechanism, it is believed that the local application of a kinase inhibitor can be used to alter chemokine expression within the skin which alters immune cell trafficking into and out of the skin leading to changes in the response to antigen deposition. The ability of EGFRIs to induce skin inflammation may involve changes in immune gene expression within cutaneous EGFR-expressing cells such as epidermal keratinocytes. The in vivo expression of major histocompatibility complex class I molecules (MHCI) on epidermal keratinocytes is increased during cancer therapy with an EGFRI in clinically inflamed skin and in skin that is clinically normal (Pollack et al., 2011).

EGFR Pathway Inhibitors

In certain embodiments, the epidermal growth factor receptor (EGFR) pathway inhibitor is a EGFR inhibitor, PI3-K inhibitor, or an AKT inhibitor, an mTOR inhibitor, a GRB2 inhibitor, SOS inhibitor, a RAS inhibitor, a MEK inhibitor, RAF inhibitor, or an ERK inhibitor.

In certain embodiments, the epidermal growth factor receptor (EGFR) pathway inhibitor is an epidermal growth factor receptor (EGFR) inhibitor or a mitogen-activated protein kinase kinase 1 (MEK1) inhibitor. In certain embodiments, it is contemplated that one may target other signal transduction pathways such as those downstream of the EGFR. This disclosure also contemplates adjuvant are inhibitors of the mitogen-activated protein kinase (MAPK) pathway.

In certain embodiments, the epidermal growth factor receptor (EGFR) inhibitor is selected from gefitinib, erlotinib, lapatinib, pelitinib, N-[4-(3-bromoanilino)quinazolin-6-yl]prop-2-enamide (PD 168393), 2-[4-(3-ethynylanilino)-7-(2-methoxyethoxy)quinazolin-6-yl]oxyethanol, aeroplysinin-1, N-(4-benzyloxyphenyl)-6,7-dimethoxy-quinazolin-4-amine, 4-[(3-bromophenyl)amino]-6,7-dimethoxyquinazoline, 4-[(3-bromophenyl)amino]-6-propionylamidoquinazoline, 4-(3-chloro-benzyl)-6,7-dimethoxy-quinazoline, (E)-N-benzyl-2-cyano-3-(3,4-dihydroxyphenyl)prop-2-enamide, N-[4-(3-bromoanilino)quinazolin-6-yl]but-2-ynamide, methyl 2,5-dihydroxycinnamate, 2',3,4,4'-tetrahydroxychalcone, N-(4-chlorophenyl)-4-(4-pyridinylmethyl)-1-phthalazinamine, 3,4-dihydroxy-α-cyanothiocinnamide, 2-[4-[4-(3-chloro-2-fluoro-anilino)-7-methoxy-quinazolin-6-yl]oxy-1-piperidyl]-N-methyl-acetamide, 4-[(3-Bromophenyl)amino]-6,7-diethoxyquinazoline, N-(3-(benzo[c][1,2,5]thiadiazol-5-ylamino)quinoxalin-2-yl)-4-methylbenzenesulfonamide, cetuximab, panitumumab, zalutumumab, nimotuzumab, matuzumab, prodrugs, derivatives, salts, or combinations thereof.

In certain embodiments, the mitogen-activated protein kinase 1 (MEK1) inhibitor is N-[(2R)-2,3-Dihydroxypropoxy]-3,4-difluoro-2-[(2-fluoro-4-iodophenyl)amino]-benzamide (PD-325901), trametinib, selumetinib, binimetinib, cobimetinib, prodrugs, derivatives, salts, or combinations thereof.

In certain embodiments, the PI3-K inhibitor is selected from wortmannin, demethoxyviridin, perifosine, idelalisib, prodrugs, derivatives, salts, and/or combinations thereof.

In certain embodiments, the AKT inhibitor is miltefosine prodrugs, derivatives, or salts thereof.

In certain embodiments, the mTOR inhibitor is rapamycin, temsirolimus, everolimus, prodrugs, derivatives, salts, and/or combinations thereof.

In certain embodiments, the RAF inhibitor is sorafenib, encorafenib, dabrafenib, vemurafenib, prodrugs, derivatives, salts, and/or combinations thereof.

Antigens and Vaccines Administration of an EGFR pathway inhibitor in conjunction with exposure to an antigen or administration of a vaccine typically enhances antigen-specific T cell immune responses. The antigen can be any type of antigen against which an immune response is desired in a subject, or any antigen to which a subject is exposed. In some cases, a subject is exposed to the antigen during an infection, such as a viral, bacterial, fungal or parasitic infection. Alternatively, the antigen can be administered to a subject, such as in the form of a vaccine. In some embodiments, the vaccine is a vaccine against a pathogen.

In some embodiments, the antigen is an antigen from a pathogen, such as a virus, bacterium, fungus or parasite. Viral pathogens include, but are not limited to retroviruses, such as human immunodeficiency virus (HIV) and human T-cell leukemia viruses; picornaviruses, such as polio virus, hepatitis A virus; hepatitis C virus, enteroviruses, human coxsackie viruses, rhinoviruses, echoviruses, and foot-and-mouth disease virus; caliciviruses, such as strains that cause gastroenteritis (e.g., Norwalk virus); togaviruses, such as alphaviruses (including chikungunya virus, equine encephalitis viruses, Sindbis virus, Semliki Forest virus, and Ross River virus) and rubella virus; flaviviruses, such as dengue viruses, yellow fever viruses, West Nile virus, St. Louis encephalitis virus, Japanese encephalitis virus, Powassan virus and other encephalitis viruses; coronaviruses, including severe acute respiratory syndrome (SARS) virus; rhabdoviruses, such as vesicular stomatitis virus and rabies virus; filoviruses, such as Ebola virus and Marburg virus); paramyxoviruses, such as parainfluenza virus, mumps virus, measles virus, and respiratory syncytial virus; orthomyxoviruses, such as influenza viruses (including avian influenza viruses and swine influenza viruses); bunyaviruses, such as Hantaan virus; Sin Nombre virus, and Rift Valley fever virus, phleboviruses and Nairo viruses; arenaviruses, such as Lassa fever virus and other hemorrhagic fever viruses, Machupo virus and Junin virus; reoviruses, such as mammalian reoviruses, orbiviurses and rotaviruses; birnaviruses; hepadnaviruses, such as hepatitis B virus; parvoviruses; papovaviruses, such as papilloma viruses, polyoma viruses and BK-virus; adenoviruses; herpesviruses, such as herpes simplex virus (HSV)-1 and HSV-2, cytomegalovirus, Epstein-Barr virus, varicella zoster virus, and other herpes viruses, including HSV-6); pox viruses, such as variola viruses and vaccinia viruses; irodoviruses, such as African swine fever virus; astroviruses; and unclassified viruses (for example, the etiological agents of spongiform encephalopathies, the agent of delta hepatitis (thought to be a defective satellite of hepatitis B virus).

Bacterial pathogens include, but are not limited to *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansai* and, *M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

Fungal pathogens include, but are not limited to *Cryptococcus neoformans, Histoplasma capsulatum, Coccidioides immitis, Blastomyces dermatitidis, Chlamydia trachomatis, Candida albicans*. Parasitic pathogens include, but are not limited to *Plasmodium falciparum, Plasmodium vivax, Trypanosoma cruzi* and *Toxoplasma gondii*.

In some embodiments, the antigen is delivered as part of a vaccine. A number of vaccines against infectious diseases are currently approved for use in the United States, examples of which are listed below.

Approved Vaccines for Immunization and Distribution in the U.S.

| Product Name | Trade Name |
| --- | --- |
| Anthrax Vaccine Adsorbed | BIOTHRAX |
| BCG Vaccine | TICE BCG |
| BCG Vaccine | MYCOBAX |
| Diphtheria & Tetanus Toxoids Adsorbed | None |
| Diphtheria & Tetanus Toxoids Adsorbed | None |
| Diphtheria & Tetanus Toxoids & Acellular Pertussis Vaccine Adsorbed | TRIPEDIA |
| Diphtheria & Tetanus Toxoids & Acellular Pertussis Vaccine Adsorbed | INFANRIX |
| Diphtheria & Tetanus Toxoids & Acellular Pertussis Vaccine Adsorbed | DAPTACEL |
| Diphtheria & Tetanus Toxoids & Acellular Pertussis Vaccine Adsorbed, Hepatitis B (recombinant) and Inactivated Poliovirus Vaccine Combined | PEDIARIX |
| Diphtheria and Tetanus Toxoids and Acellular Pertussis Adsorbed and Inactivated Poliovirus Vaccine | KINRIX |
| Diphtheria and Tetanus Toxoids and Acellular Pertussis Adsorbed, Inactivated Poliovirus and Haemophilus b Conjugate (Tetanus Toxoid Conjugate) Vaccine | PENTACEL |
| Haemophilus b Conjugate Vaccine (Diphtheria CRM197 Protein Conjugate) | HIBTITER |
| Haemophilus b Conjugate Vaccine (Meningococcal Protein Conjugate) | PEDVAXHIB |
| Haemophilus b Conjugate Vaccine (Tetanus Toxoid Conjugate) | ACTHIB |
| Haemophilus b Conjugate Vaccine (Meningococcal Protein Conjugate) & Hepatitis B Vaccine (Recombinant) | COMVAX |
| Hepatitis A Vaccine, Inactivated | HAVRIX |
| Hepatitis A Vaccine, Inactivated | VAQTA |
| Hepatitis A Inactivated and Hepatitis B (Recombinant) Vaccine | TWINRIX |
| Hepatitis B Vaccine (Recombinant) | RECOMBIVAX HB |
| Hepatitis B Vaccine (Recombinant) | ENGERIX-B |
| Human Papillomavirus (Types 6, 11, 16, 18) Recombinant Vaccine | GARDASIL |

-continued

| Product Name | Trade Name |
| --- | --- |
| Influenza Virus Vaccine | AFLURIA |
| Influenza Virus Vaccine, H5N1 | None |
| Influenza Virus Vaccine, Trivalent, Types A and B | FLULAVAL |
| Influenza Virus Vaccine, Live, Intranasal | FLUMIST |
| Influenza Virus Vaccine, Trivalent, Types A and B | FLUARIX |
| Influenza Virus Vaccine, Trivalent, Types A and B | FLUVIRIN |
| Influenza Virus Vaccine, Trivalent, Types A and B | FLUZONE |
| Japanese Encephalitis Virus Vaccine Inactivated | JE-VAX |
| Measles Virus Vaccine, Live | ATTENUVAX |
| Measles and Mumps Virus Vaccine, Live | M-M-Vax |
| Measles, Mumps, and Rubella Virus Vaccine, Live | M-M-R II |
| Measles, Mumps, Rubella and Varicella Virus Vaccine, Live | PROQUAD |
| Meningococcal Polysaccharide (Serogroups A, C, Y and W-135) Diphtheria Toxoid Conjugate Vaccine | MENACTRA |
| Meningococcal Polysaccharide Vaccine, Groups A, C, Y and W-135 Combined | MENOMUNE-A/C/Y/W-135 |
| Mumps Virus Vaccine Live | MUMPSVAX |
| Plague Vaccine | None |
| Pneumococcal Vaccine, Polyvalent | PNEUMOVAX 23 |
| Pneumococcal 7-valent Conjugate Vaccine (Diphtheria CRM197 Protein) | PREVNAR |
| Poliovirus Vaccine Inactivated (Human Diploid Cell) | POLIOVAX |
| Poliovirus Vaccine Inactivated (Monkey Kidney Cell) | IPOL |
| Rabies Vaccine | IMOVAX |
| Rabies Vaccine | RABAVERT |
| Rabies Vaccine Adsorbed | No Trade Name |
| Rotavirus Vaccine, Live, Oral | ROTARIX |
| Rotavirus Vaccine, Live, Oral, Pentavalent | ROTATEQ |
| Rubella Virus Vaccine Live | MERUVAX II |
| Smallpox (Vaccinia) Vaccine, Live | ACAM2000 |
| Smallpox Vaccine, Dried, Calf Lymph Type | DRYVAX |
| Tetanus & Diphtheria Toxoids Adsorbed for Adult Use | None |
| Tetanus & Diphtheria Toxoids Adsorbed for Adult Use | DECAVAC |
| Tetanus & Diphtheria Toxoids Adsorbed for Adult Use | TENIVAC |
| Tetanus Toxoid | None |
| Tetanus Toxoid Adsorbed | None |
| Tetanus Toxoid Adsorbed | None |
| Tetanus Toxoid, Reduced Diphtheria Toxoid and Acellular Pertussis Vaccine, Adsorbed | ADACEL |
| Tetanus Toxoid, Reduced Diphtheria Toxoid and Acellular Pertussis Vaccine, Adsorbed | BOOSTRIX |
| Typhoid Vaccine Live Oral Ty21a | VIVOTIF |
| Typhoid Vi Polysaccharide Vaccine | TYPHIM VI |
| Varicella Virus Vaccine Live | VARIVAX |
| Yellow Fever Vaccine | YF-VAX |
| Zoster Vaccine, Live | ZOSTAVAX |

In certain embodiments, compositions disclosed herein are used as vaccines that contain a viral medium such as virus which is live, killed or attenuated, or a virus particle or virosome comprising a live, killed or attenuated, or a virus-like particle that does not contain viral nucleic acids or intact viral nucleic acids, or a polypeptide sequence expressed by a virus, e.g., polypeptide sequence is a viral envelope protein or matrix protein.

The viral medium can be used directly in vaccine formulations, or lyophilized, as desired, using lyophilization protocols well known to the artisan. Lyophilized virus will typically be maintained below room temperature. When ready for use the lyophilized viral medium is reconstituted in a stabilizing solution, e.g., saline or comprising SPG, Mg, and HEPES, with or without adjuvant.

In certain embodiments, compositions comprising EGFR pathway inhibitors and vaccines of the disclosure contain as an active ingredient in an immunogenetically effective amount. The viral medium may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a composition as described herein, via aerosol, droplet, oral, topical or other route, the immune system of the subject responds to the vaccine by producing antibodies specific for antigenic proteins, e.g., viral envelope or matrix proteins. As a result of the vaccination the host becomes at least partially or completely immune to viral infection, or resistant to developing moderate or severe viral infection, e.g., in the lower respiratory tract.

The subject to which the vaccine and inhibitor are administered can be any mammal which is susceptible to infection by viral infections and which the subject is capable of generating a protective immune response to the antigens. Thus, suitable subjects include humans, non-human primates, bovine, equine, swine, rodents, etc. Accordingly, the disclosure relates to vaccines compositions and methods for human and veterinary uses.

In certain embodiments, the vaccines and inhibitors of the disclosure are administered to a subject susceptible to or otherwise at risk of infection to enhance the subject's own immune response capabilities. Such an amount is defined to be an "immunogenically effective dose." In this use, the precise amounts again depend on the subject's state of health and weight, the mode of administration, the nature of the formulation.

In some instances it may be desirable to combine the inhibitors with multiple viral components of the disclosure with multiple vaccines which induce protective responses to multiple antigens, e.g., multiple viruses or attenuated viral strains or multiple polypeptide antigens.

Single or multiple administrations of the compositions of the disclosure can be carried out. In neonates and infants, multiple administrations may be required to elicit sufficient levels of immunity. Administration may begin within the first month of life, and at intervals throughout childhood, such as at two months, six months, one year and two years, as necessary to maintain sufficient levels of protection against native (wild-type) infection. Similarly, adults who are particularly susceptible to repeated or serious infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection.

EXAMPLES

Cells and Virus Stocks

Madin-Darby canine kidney (MDCK) cells (CCL 34, ATCC, Manassas, Va.) were maintained in Dulbecco's Modified Eagle's Medium (Mediatech, Herndon, Va.) containing 10% fetal bovine serum (Hyclone, Thermo Scientific, Rockford, Ill.). Influenza virus stocks (A/California/07/09 (H1N1)) were propagated in MDCK cells and purified with sucrose gradient centrifugation. The purity of the virus was determined by SDS PAGE followed by Coomassie blue staining. For inactivation, the purified virus was treated with formalin at a final concentration of 0.1% (vol/vol), incubated for 72 h at 4° C., and then dialyzed against PBS buffer. Inactivation of virus was confirmed by plaque assay in MDCK cells. The hemagglutination (HA) activity was determined using turkey blood cells (LAMPIRE, Pipersville, Pa.) (WHO/CDS/CSR/NCS (2002) WHO Manual of Animal Influenza Diagnosis and Surveillance). Mouse-adapted virus was obtained by serially passaging in lungs of BALB/c mice and titers were determined by plaque assay. The $LD_{50}$ was determined using Reed-Munch formula.

Immunizations, Challenge and Sample Collection

Six- to eight-week-old female BALB/c mice were purchased from Harlan Laboratories (Tampa, Fla.) and housed at Emory University Whitehead Animal Facility. Mice (5 per group) were anesthetized by intraperitoneal injection of xylazine/ketamine cocktail to remove dorsal hair. On the day of immunization 40 µl of 4 mM PD168393 (VWR International, Dallas, Tex.) or vehicle (DMSO and ethanol/negative control) were applied topically on the shaved skin and allowed to dry for 10 min prior to intradermal injection of 50 µl of vaccine (2 µg total protein) or PBS (negative control) in the same area. Animals were bled sub-mandibularly at weeks 2, 4 and 8 after immunization under systemic anesthesia while spleens and inguinal lymph nodes were collected at weeks 1 and 2 for evaluation of cellular immune responses (FIG. 1a). Lungs were collected on day 4 post-infection and lung homogenates were stored in DMEM and the protease inhibitor phenylmethylsulfonyl fluoride (1 mM) (Sigma, St. Louis, Mo.) at −20° C. until assayed for viral titers. Inguinal lymph nodes and spleens were processed similarly into single cell suspensions in complete RPMI1640 for cytokine determination. Tissue samples were treated with red blood cell lysis buffer after their initial processing (Sigma, St. Louis, Mo.). For challenge, mice were infected intranasally under isoflurane anesthesia with $25 \times LD_{50}$ (47 PFU) mouse adapted virus 9 weeks after their vaccination and monitored for 14 days for body weight changes, fever, hunched posture, and mortality. Weight loss exceeding 25% was used as the experimental end point, at which mice were euthanized according to IACUC guidelines. All studies were approved by Emory University's Institutional Animal Care and Use Committee.

Humoral Immune Responses

Virus-specific antibody levels were determined by ELISA. Hemagglutination inhibition titers (HAI) were assessed using the WHO protocol. Neutralizing antibody titers were determined in heat inactivated sera by microneutralization assay using 100 $TCID_{50}$/well of A/California/07/2009 virus. (Koutsonanos et al., 2012).

Cellular Immune Responses and Post-Challenge Lung Titers

Freshly isolated splenocytes and lymphocytes ($1.0 \times 10^6$/200 µl cRPMI) were cultured for 36-48 h in the presence of 4 µg/ml vaccine to enumerate IL-4 and IFN-γ ELISPOT secreting cells. ELISPOT reagents were purchased from BD-PharMingen (San Jose, Calif.). Enumeration of vaccine-specific ASC was carried out by ELISPOT assay and counted using an ELISPOT reader and counter (Cellular Technologies, Shaker Heights, Ohio).

Lung homogenates were prepared in DMEM and viral titers were assessed per gram of tissue by plaque assay reported in Sha and Compans, J Virol, 2000, 74:4999-5005.

Topical PD168393 Application Alters CCL2 Expression within the Skin.

Figure 5:
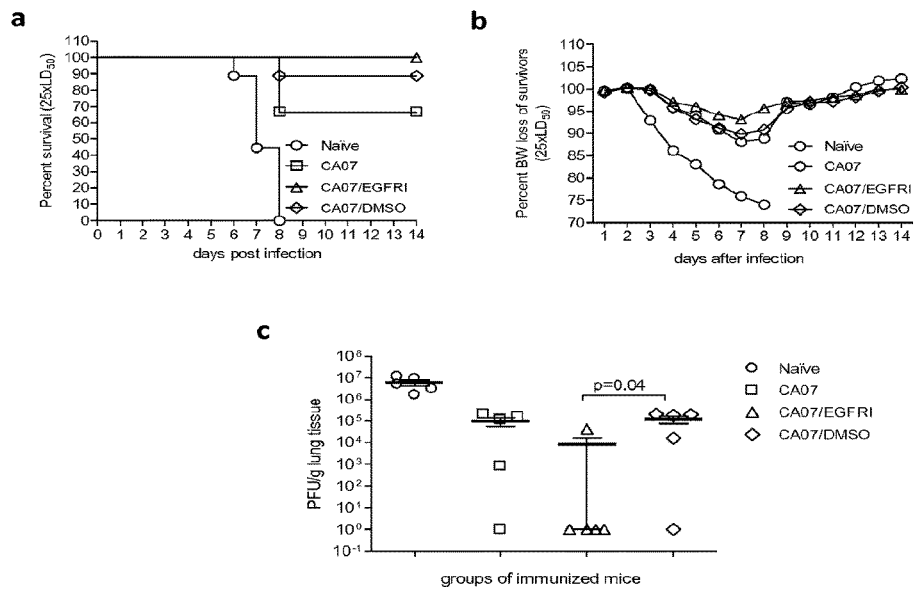
FIG. 5 shows data indicating topical application of an EGFRI at the site of vaccination can enhance the protective immunity elicited by cutaneous vaccination. EGFR inhibitor-vaccinated mice had less detectable virus in their lungs, less influenza-induced weight loss, and improved survival compared to vehicle-vaccinated mice and mice receiving the vaccine alone.
Figure 6:
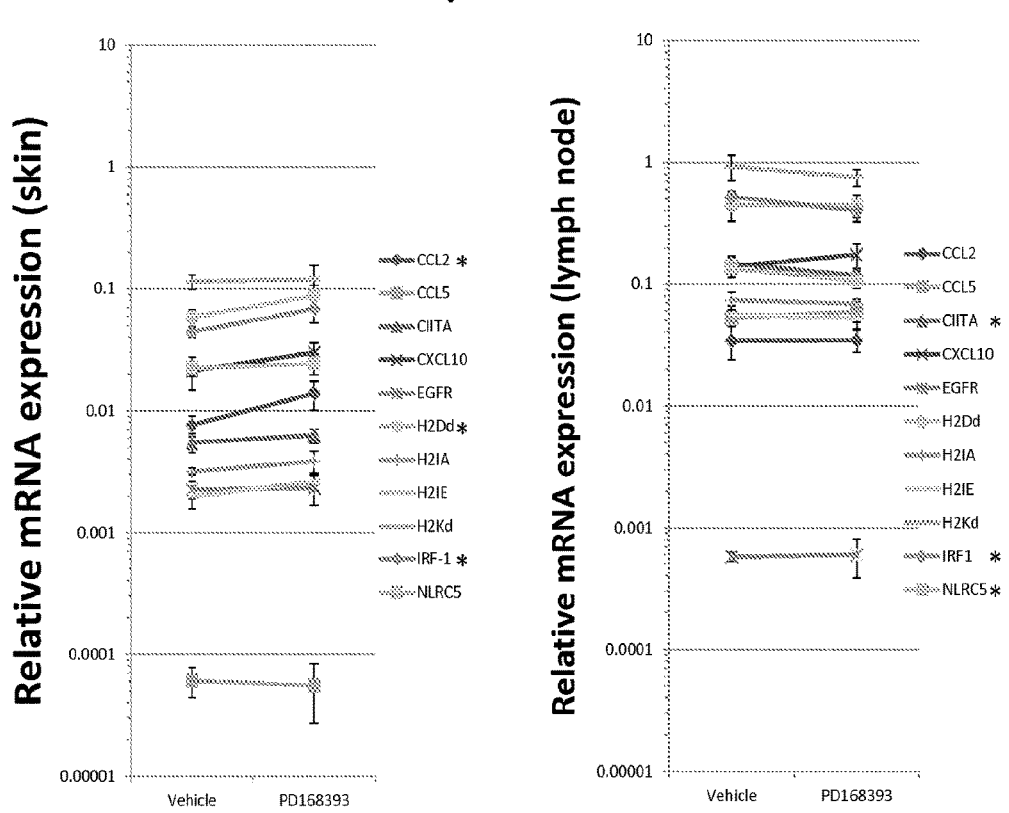
FIG. 6 shows data indicating the topical application of the EGFR inhibitor to the dorsal skin of Balb/C mice lead to a statistically significant increase in steady state mRNA levels of the chemokine CCL2.

The topical application of the irreversible EGFR inhibitor PD168393 can enhance the elicitation phase of contact hypersensitivity in a manner that is associated with increases in several chemoattractant chemokines. During EGFRI therapy there are changes in immune gene expression even in clinically normal (non-inflamed) skin). To determine how EGFR inhibition alters immune gene expression, PD168393 or vehicle (10% DMSO in ethanol) was applied to the backs of Balb/c mice (5 mice per group) and steady state mRNA levels of several genes were measured. A six hour time point was selected for these experiments. As shown in FIG. 5, the topical application of PD168393 to the dorsal skin of Balb/C mice lead to a statistically significant increase in steady state mRNA levels of the chemokine CCL2 (also known as monocyte chemoattractant protein (MCP)-1). This increase was observed independent of the reference housekeeping gene used in the analysis. In contrast, steady state levels of the housekeeping genes and several other genes analyzed were unchanged by topical PD168393 at this time point. These studies indicate that a single application of an EGFRI to mouse skin can alter the expression of chemokines that are known to influence immune cell trafficking into the skin.

Topical Application of an EGFRI Enhances Humoral Responses to Influenza Vaccination The impact of EGFRI treatment on the humoral response to vaccination was examined. Serum collected from mice immunized after topical application of an EGFRI (PD168393) or vehicle was assessed for hemagglutination inhibition (HAI) and neutralizing antibody (NT) titers both of which are considered correlates of influenza-vaccine induced protective immunity. As an additional control, mice that received only the vaccination without any topical treatments were included. As shown in FIG. 1, a single application of PD168393 at the site of and just prior to vaccination induced significantly higher HAI titers than those mice where vehicle was applied prior to vaccination and mice that received only the vaccine (no topical treatment). The HAI titers rose more rapidly in the vaccine/EGFRI group achieving two-fold higher differences than the vaccine alone or vehicle-vaccine group as early as week 4 (FIGS. 1c and 1d). With regards to the NT titers, while the vehicle-vaccinated mice had lower NT titers than mice that received vaccine alone, the titers seen in the EGFRI-vaccinated mice were increased relative to both control groups by week 8. In contrast to these findings, no differences were observed between the three groups using assays that measure total vaccine-reactive antibodies. These data indicates that a single topical application of an EGFRI can influence the generation of functionally relevant antibodies while not altering the total amount of antibodies induced by vaccination.

Figure 3:
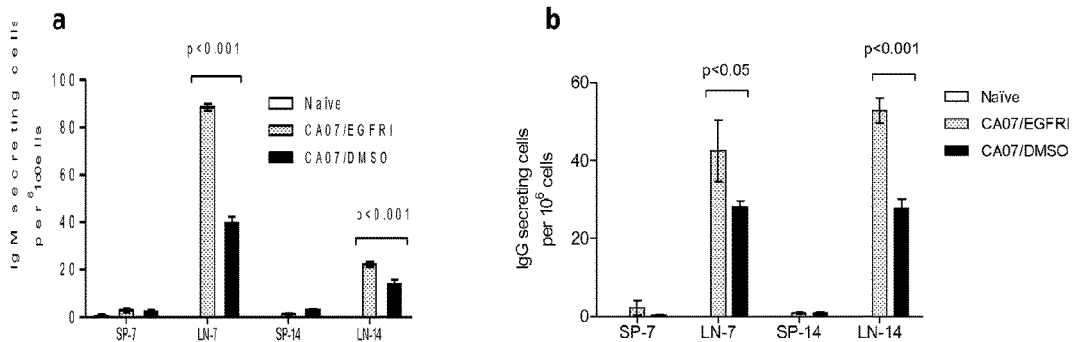
FIG. 3 shows data indicating topical treatment of an EGFR inhibitor prior to vaccination induces an increase in the number of cells producing influenza-specific antibodies within skin-draining lymph nodes.

Topical Application of an EGFRI Induces Increased Numbers of Vaccine-Specific Antibody Secreting Cells in Local Lymph Nodes In order to determine how the application of an EGFRI impacts events in skin-draining lymph nodes following vaccination, vaccine-specific IgM-secreting cells and IgG-secreting cells were measured in the skin draining lymph nodes (and the spleen) at one week and two weeks post vaccination. At seven days post vaccination, EGFRI-vaccinated mice had double the number of IgM secreting cells as compared to vehicle-vaccinated mice ($p<0.001$) (FIG. 3a). At both 1 and 2 weeks post vaccination, the EGFRI-vaccinated mice had significantly higher numbers of IgG-secreting cells as compared to vehicle-vaccinated mice (FIG. 3b). Further, in contrast to vehicle-vaccinated mice, the number of IgG secreting cells increased from day 7 to day 14 post vaccination in the EGFRI-vaccinated group to the point where it was twice as high as vehicle-vaccinated mice by day 14 ($p<0.001$) (FIG. 3b). In contrast to these differences in the local immune response, cellular responses in the spleen were low in comparison and without any notable differences between EGFRI- and vehicle-vaccinated mice.

Topical Application of an EGFRI Increases Cytokine Production in Skin Draining Lymph Nodes of Vaccinated Mice.

Figure 4:
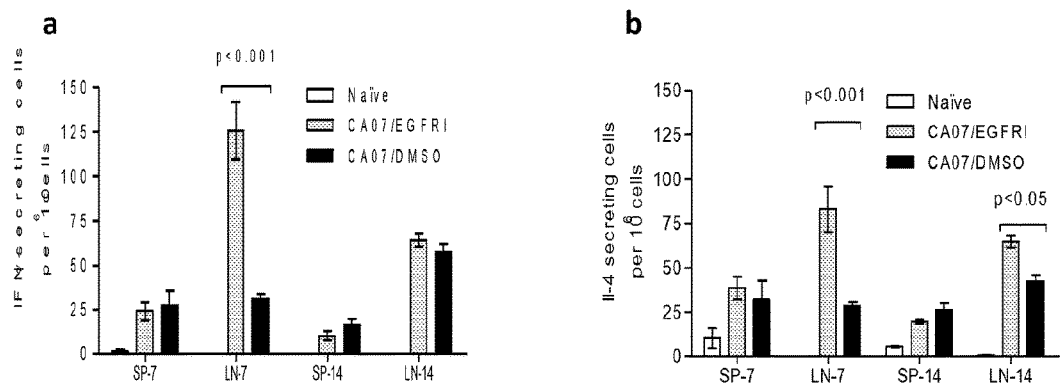
FIG. 4 shows data indicating in EGFR inhibitor-vaccinated mice, there were provided higher numbers of activated influenza-specific immune cells as defined by IFN-γ and IL-4 secretion compared to vehicle-vaccinated mice at one week post immunization.

To assess the impact of the EGFRI on cytokine production and immune cell activation, levels of IFN-γ-producing and IL-4-producing cells were measured in the skin-draining lymph nodes and spleens of vaccinated mice at one and two weeks post vaccination. In EGFRI-vaccinated mice there were 3-fold higher numbers of IL-4 secreting cells compared to vehicle-vaccinated mice at one week post immunization (FIG. 4a). At two weeks post immunization, the levels of IL-4 secreting lymphocytes remained significantly higher in the EGRI treated group ($p<0.05$). There was a 4-fold increase in the numbers of IFN-γ secreting cells in the vaccine-EGFRI group as compared to the vaccine-vehicle cohort one week post-vaccination though this difference was absent by two weeks post vaccination (FIG. 4b). Again, in spleens the numbers of these cells were low and no differences between EGFRI- and vehicle-vaccinated mice were found.

Topical Application of an EGFRI Prior to Vaccination Increases Protective Immunity.

To determine the impact of the EGFRI on vaccine-mediated protection against viral challenge, nice weeks following vaccination mice were challenged with $25 \times LD_{50}$ of mouse adapted homologous influenza virus. While all mice suffered weight losses with a maximum around day 7 post-challenge, EGFRI-vaccinated mice had the least amount of weight loss (FIG. 5a). In line with these findings, an analysis of pulmonary viral loads revealed that EGFRI-vaccinated mice had less detectable virus in their lungs compared to vehicle-vaccinated mice and mice receiving the vaccine alone (FIG. 5b). These results support the notion that the topical application of an EGFRI at the site of vaccination can enhance the protective immunity elicited by cutaneous vaccination.

What we claim:

1. A method of vaccinating a subject comprising administering a viral vaccine in combination with N-[4-(3-bromoanilino)quinazolin-6-yl]prop-2-enamide or salt thereof locally to the skin of a subject in need thereof,
    wherein the viral vaccine comprises a live, killed, or attenuated virus, a virus particle, virus-like particle, or virosome, and
    wherein virus-specific neutralizing antibodies are formed in serum of the subject.

2. The method of claim 1 wherein administered locally to the skin is topically administered or intradermally administered.

3. The method of claim 1, wherein viral vaccine is an influenza vaccine.

* * * * *